(12) United States Patent
Matsuo et al.

(10) Patent No.: US 9,090,939 B1
(45) Date of Patent: Jul. 28, 2015

(54) SYSTEM AND METHOD FOR PERIPHERAL DEVICE DETECTION ON MOBILE HANDSET SERIAL PORT

(75) Inventors: Kotaro Matsuo, Poway, CA (US); Yasuhiro Ito, Oota-ku (JP)

(73) Assignee: KYOCERA Corporation, Kyoto (JP)

( * ) Notice: Subject to any disclaimer, the term of this patent is extended or adjusted under 35 U.S.C. 154(b) by 1661 days.

(21) Appl. No.: 11/696,109

(22) Filed: Apr. 3, 2007

(51) Int. Cl.
*H04B 1/00* (2006.01)
*C12Q 1/68* (2006.01)

(52) U.S. Cl.
CPC ........ *C12Q 1/6883* (2013.01); *C12Q 2600/106* (2013.01); *C12Q 2600/156* (2013.01)

(58) Field of Classification Search
CPC ........... C12Q 1/6883; C12Q 2600/106; C12Q 2600/156
USPC ............... 455/556.1, 575.6, 90.2, 557, 186.1, 455/414.1, 432.2; 705/1; 713/155; 709/217
See application file for complete search history.

(56) References Cited

U.S. PATENT DOCUMENTS

| | | | |
|---|---|---|---|
| 6,586,046 B1 | 7/2003 | Ackerman et al. | |
| 6,829,481 B2 | 12/2004 | Souissi | |
| 7,079,865 B1 * | 7/2006 | Farazmandnia et al. | 455/557 |
| 2005/0070276 A1 * | 3/2005 | McGarry | 455/432.2 |
| 2006/0258342 A1 * | 11/2006 | Fok et al. | 455/414.1 |
| 2006/0277308 A1 * | 12/2006 | Morse et al. | 709/227 |
| 2008/0097775 A1 * | 4/2008 | Kim | 705/1 |

* cited by examiner

*Primary Examiner* — Kumar Patel
*Assistant Examiner* — Kuo Woo

(57) ABSTRACT

A device and method for providing a portable wireless communication device having an external device interface, and which is capable of intelligently configuring itself to operate according to one of a plurality of operating modes according to the needs of an individual user are disclosed. An exemplary device comprises an interface configured to communicatively couple the portable wireless communication device with an external device, and circuitry configured to record an instance of a first operation configuration, detect a coupled external device, predict a most likely next operation mode responsive to recording the instance of the first operation configuration, configure the portable wireless communication device to operate according to a first operating mode in response to the predicted the most likely next operation mode, and communicate with the external device.

9 Claims, 4 Drawing Sheets

SYSTEM AND METHOD FOR PERIPHERAL DEVICE DETECTION ON MOBILE HANDSET SERIAL PORT

FIELD OF THE INVENTION

This invention generally relates to portable electronic devices and, more particularly, to a portable wireless communication device with multiple methods of communicating with other devices.

BACKGROUND OF THE INVENTION

Portable wireless communication devices, such as cell phones, PDAs, and the like, have become increasingly more powerful with a growing number of features. In particular, portable wireless communication devices are becoming more complex with multiple modes of interacting with other devices. For example, many portable wireless communication devices currently may operate as a communications device and as data transfer device.

With the advances in information storage technology, portable wireless communication devices may also operate in a mass storage mode, wherein the portable wireless communication device may view an external device as a memory storage area, or the external device may view the portable wireless communication device as a memory storage device.

In addition, with the convergence of multi-media capabilities into portable wireless communication devices, portable wireless communication devices may use external devices as a media player, or may themselves be used by external devices as media players. Moreover, when augmented by the integration of digital rights management capabilities, portable wireless communication devices may operate in a digital rights management mode, wherein the portable wireless communication device may be used to securely play, store, or transfer media content such as digital music, digital video, and other protected media, as well as protected electronic files and software applications.

Accordingly, support for three or more varying modes of operation are becoming a necessity for many portable wireless communication devices. For example, three typical modes are: communications (COM) mode, mass storage (MS) mode, and digital rights management (DRM) mode.

In response to the greater number of operating modes available, portable wireless communication devices often must also be able to interface with a plurality of external devices.

One technique for interfacing with a plurality of external devices is for the portable wireless communication device to provide a plurality of interfaces wherein a user may plug an external device into an interface dedicated to a particular mode of operation. For example, a portable wireless communication device may use a proprietary interface for instances of being used in communications mode, and use a universal interface, such as a USB port, for instances of being used in digital rights management mode. However, as the number of modes of operation increase, the increasing the number of physical interfaces undesirably detracts from a device's ability to retain a compact form facto and increases costs.

Another technique is to use a single universal hardware interface for multiple operation methods. However, this technique would still require the user to configure the portable wireless communication device to operate in a particular mode, according to which external device it is coupled to, leading to complexity of operation and an unsatisfactory user experience.

Accordingly, there exists a strong need in the art for a system and method for peripheral device detection on a mobile handset serial port which addresses the above deficiencies.

SUMMARY OF THE INVENTION

In one embodiment, a wireless communication device includes a single external device interface, and is capable of efficiently and intelligently configuring itself to operate according to one of a plurality of operating modes according to the needs of an individual user.

In one embodiment, a predictor module is capable of ascertaining or learning how a particular user usually uses his mobile station interface port. According to one embodiment, the invention will then automatically configure the port settings (e.g., USB port) to the configuration the port is most likely to be used.

According to one embodiment, an automated method of managing at least three modes in a portable wireless communication device comprises: (1) Detecting whether a client device (the external device) requires COM mode support; (2) Checking whether a host device (the portable wireless communication device) has mass storage support; (3) Checking whether the host device has DRM support.

According to one embodiment of the invention, the invention provides for automatic installation of a driver through first checking whether a external client device is connected or not, and for checking for proper memory availability.

According to one embodiment of the invention, the default order for selection of an operation mode may be: first COM mode, second Mass Storage mode, and third DRM mode. This is an efficient solution due to the likelihood the host device (handset) will be used by an external client (PC) according to the respective modes will decrease accordingly, and with this order less iterations/search operations will occur.

According to one embodiment of the invention, the invention provides for intelligently predicting a most likely next operation mode of a particular user, and configuring the portable wireless communication device in response to the predicted the most likely next operation mode.

The benefits of these various embodiment may include the ability for the portable wireless communication device to properly select a correct operation mode with minimal user interaction. Solution logic can be implemented either on the portable wireless communication device, the external device, or a combination of both. In reducing the user's interaction in configuring, the invention aims to improve the user's overall experience of the device.

DETAILED DESCRIPTION OF THE INVENTION

Figure 1:
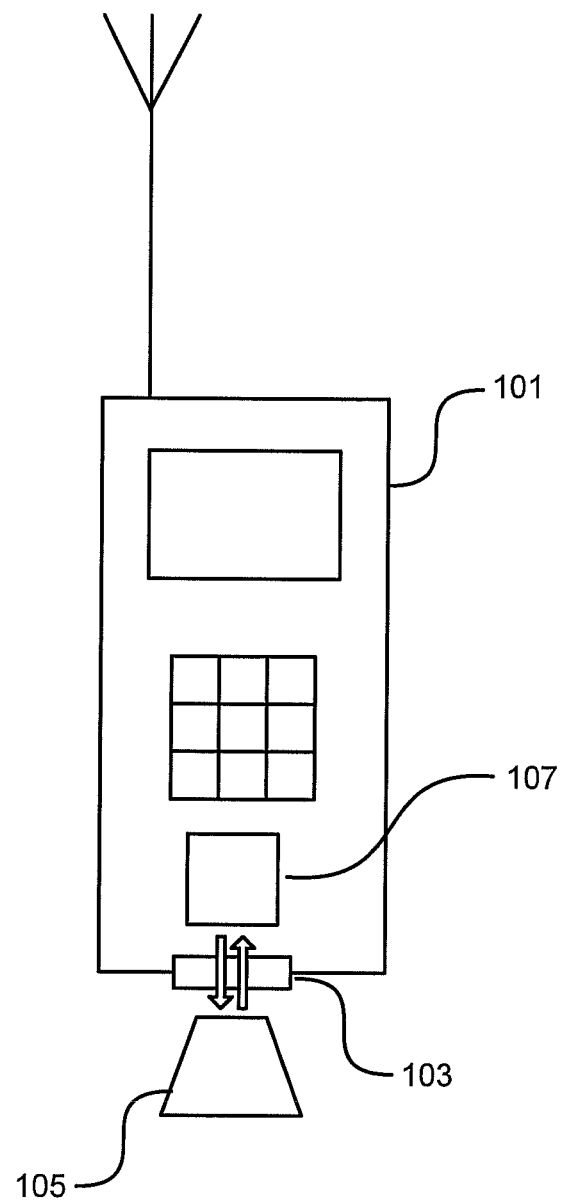
FIG. 1 depicts a portable wireless communication device having a plurality of operating modes according to one embodiment of the present invention.

Referring to FIG. 1, a portable wireless communication device 101 having a plurality of operating modes according to one embodiment of the present invention is shown. Although the wireless communication device is illustrated as a mobile phone, the portable wireless communication device is not limited to this particular embodiment. For example, other examples of wireless communication devices may include PDAs, personal computers, media players, and other portable electronic devices. For brevity, typical elements of a portable wireless communication device, such as a transceiver coupled to an antenna along with other hardware and software components for sending and receiving wireless signals will not be described in detail herein.

As shown in FIG. 1, portable wireless communication device 101 having a plurality of operating modes comprises an interface 103 configured to communicatively couple portable wireless communication device 101 with an external device 105, and circuitry 107 configured to detect coupled external device 105, interrogate portable wireless communication device 101 in response to the detecting coupled external device 105, and to configure portable wireless communication device 101 to operate according to a first operating mode.

Interface 103 is schematically illustrated as a physical interface, which may include, for example, USB, firewire, serial, PCI, PCMCIA, proprietary, and other physical interfaces. However, interface 103 is not limited to physical interfaces. Accordingly, interface 103 may be a wireless interface, such as Bluetooth, IR, wireless USB, IEEE unlicensed, etc., so long as interface 103 provides for external device 105 to be communicably coupled with portable wireless communication device 101.

Similarly, external device 105 is not specifically limited to any particular category or class of device. External device 105 may be any device that makes use of the functionality of portable wireless communication device 101, or which portable wireless communication device 101 may utilize. For example, external device 105 may include PDAs, personal computers, media players, and other electronic devices, as well as accessories to portable wireless communication device 101.

By way of example, circuitry 107 may comprise a microprocessor, which may be embodied as a single structure, or as discrete elements. Circuitry 107 is not limited to hardware and may be a combination of hardware and software for carrying out the functions described herein.

Figure 2:
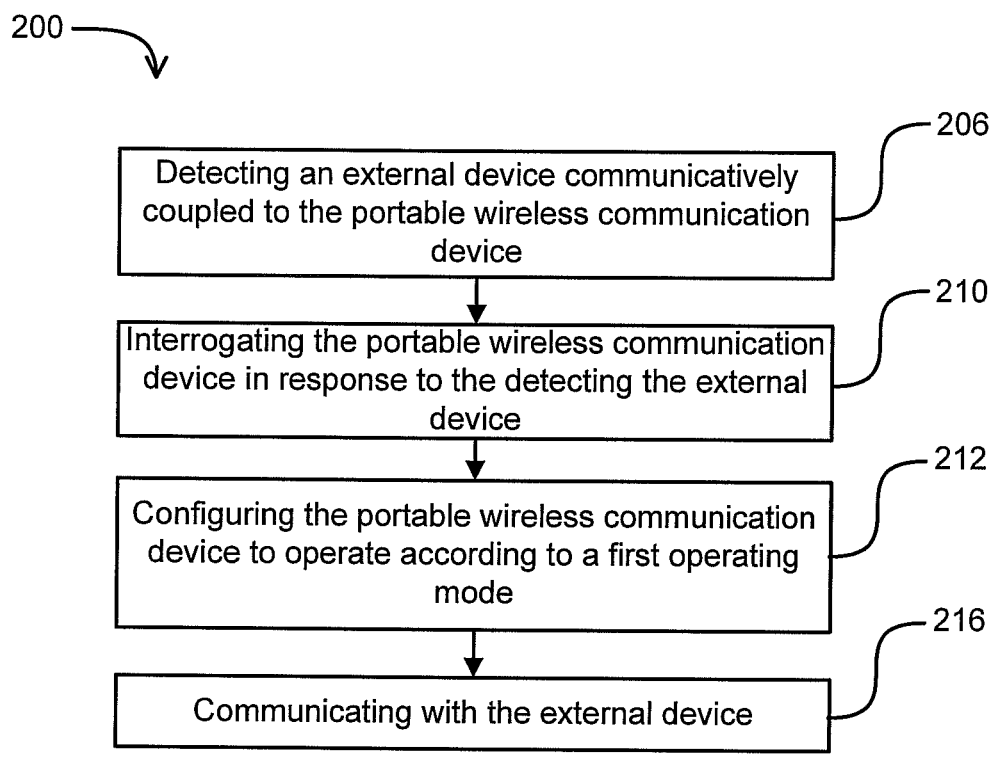
FIG. 2 depicts a method for managing a portable wireless communication device having a plurality of operating modes according to one embodiment of the present invention.

Referring to FIG. 2, a method 200 for managing a portable wireless communication device having an interface, and configurable to operate in a plurality of operating modes according to one embodiment of the present invention is shown. According to this embodiment, the portable wireless communication device, capable of operating according to a plurality of modes, can automatically configure itself to operate according to a first operating mode. This automatic self-configuration may be accomplished using default values or an adaptive learning technique, as discussed below.

In particular, method 200 includes detecting 206 an external device communicatively coupled to the portable wireless communication device, the external device being communicatively, coupled through an interface, configuring 212 the portable wireless communication device to operate according to a first operating mode, and communicating 216 with the external device.

As illustrated in FIG. 1 and as discussed above, the external device may be communicatively coupled with the portable wireless communication device through the interface through a variety of techniques, physical and otherwise. As such, the interface may serve to communicate to the portable wireless communication device that the external device has been coupled. Accordingly, the portable wireless communication device may use this communication to detect 206 whether or not the external device is coupled.

Detecting 206 of the external device may be through active or passive techniques. According to one embodiment, the portable wireless communication device may actively signal a coupled external device to provoke a response, which in turn may indicate that the external device is communicably coupled to the portable wireless communication device. According to another embodiment, the portable wireless communication device may passively listen for a signal from a coupled external device, which in turn may indicate that the external device is communicably coupled to the portable wireless communication device. The signaling between the portable wireless communication device and the coupled external device may be sent via a physical or wireless connection.

Furthermore, in both cases, the portable wireless communication device may detect 206 the coupled external device by explicitly receiving a signal to that effect, or by indirectly determining its presence. There are numerous techniques contemplated for indirectly detecting the coupled external device, for example, in the case of a physical coupling, the portable wireless communication device may detect its coupling by detecting a draw of power (e.g., through a USB connection), and in the case of a wireless coupling, the portable wireless communication device may detect its coupling by the establishment of a secure link (e.g., Bluetooth pairing).

In addition, detection 206 of the external device may also include determining whether the external device requires communication support. For example, this determination may be made where the external device is configured to use the portable wireless communication device as a modem. This determination may also be made where the external device is a dedicated accessory of the portable wireless communication device. By making this determination during detection 206 the portable wireless communication device may configure itself, or remain configured, to operate as a communication device without considering operation in other modes.

Method 200 for managing a portable wireless communication device further includes the portable wireless communication device interrogating 210 itself for predetermined functionality. According to one embodiment, interrogation 210 may be done in response to the detection of the coupled external device. In interrogating 210 itself, the portable wireless communication device may allow for automatic installation of a driver or other configuration in a predictive manner. Moreover, interrogation 210 may provide for a default setting when used in conjunction with a more active learning technique.

Continuing with reference to FIG. 2, the method 200 for managing a portable wireless communication device includes configuring 212 the portable wireless communication device to operate according to a first operating mode. By way of illustration, examples of operating modes include: Communications mode (COM mode), Mass Storage mode (MS mode), Digital Rights Management mode (DRM mode), etc. To further describe the exemplary operating modes, while operating in COM mode, the portable wireless communication device may remain configured to be used as a communication device. Also, while in COM mode, the portable wireless communication device may be further configured to operate with an accessory (DIAG mode) or to provide data communications (DATA mode). As an accessory, the portable wireless communication device may operate as a modem for the external device.

While operating in MS mode, the portable wireless communication device, may operate as an electronic storage device. In other words, the communicatively coupled external device may store information on the portable wireless communication device. This storage may be in such a way that the external device treats the portable wireless communication device as separate storage drive or, in the alternate, the external device treats the portable wireless communication device's storage capability as integrated with any memory capability the external device may have.

Also, while operating in MS mode, and when the portable wireless communication device is further coupled to an external memory (e.g, SD memory card), the portable wireless communication device may be further configured to operate as an electronic storage device wherein information is stored on the external memory, as distinguished from the integrated memory of the portable wireless communication device itself. As above, the communicatively coupled external device may treat the external memory as a separate or an integrated storage.

While operating in DRM mode, the portable wireless communication device, may operate to transfer protected content without compromising the contents protection. Common examples of protected content include digital music files, digital video files, encrypted electronic presentations, and proprietary software applications.

Operating in DRM mode, the communicatively coupled external device may securely transfer the protected content onto the portable wireless communication device. The content may then be stored, executed, and/or communicated to another location.

To illustrate, when in DRM mode, an external media player may download purchased .mp3 files such that the purchased .mp3 files may be played on the portable wireless communication device. According to another embodiment, the .mp3 files may be saved onto the portable wireless communication device. According to another embodiment, the mp3 files may be transferred to third device. In all three illustrated cases, the portable wireless communication device provides for the transfer of the purchased .mp3 file without compromising its content and preventing access by unauthorized parties.

As shown in the above illustrations, one skilled in the art will recognize that many operating modes are possible. As the operating modes described above are non-limiting, and other modes are contemplated, any operating mode having a unique driver or requiring a particular configuration is contemplated by the present invention.

Once the portable wireless communication device has been configured to operate according to a first operating mode, the portable wireless communication device may communicate 216 with the external device. Communicating, as used here is not to be construed in any limiting way. Communication may include unilateral as well as multi-directional signaling. As used here, communication means that the interactions between the portable wireless communication device and the coupled external device will proceed as intended, according to a desired operation mode.

Figure 3:
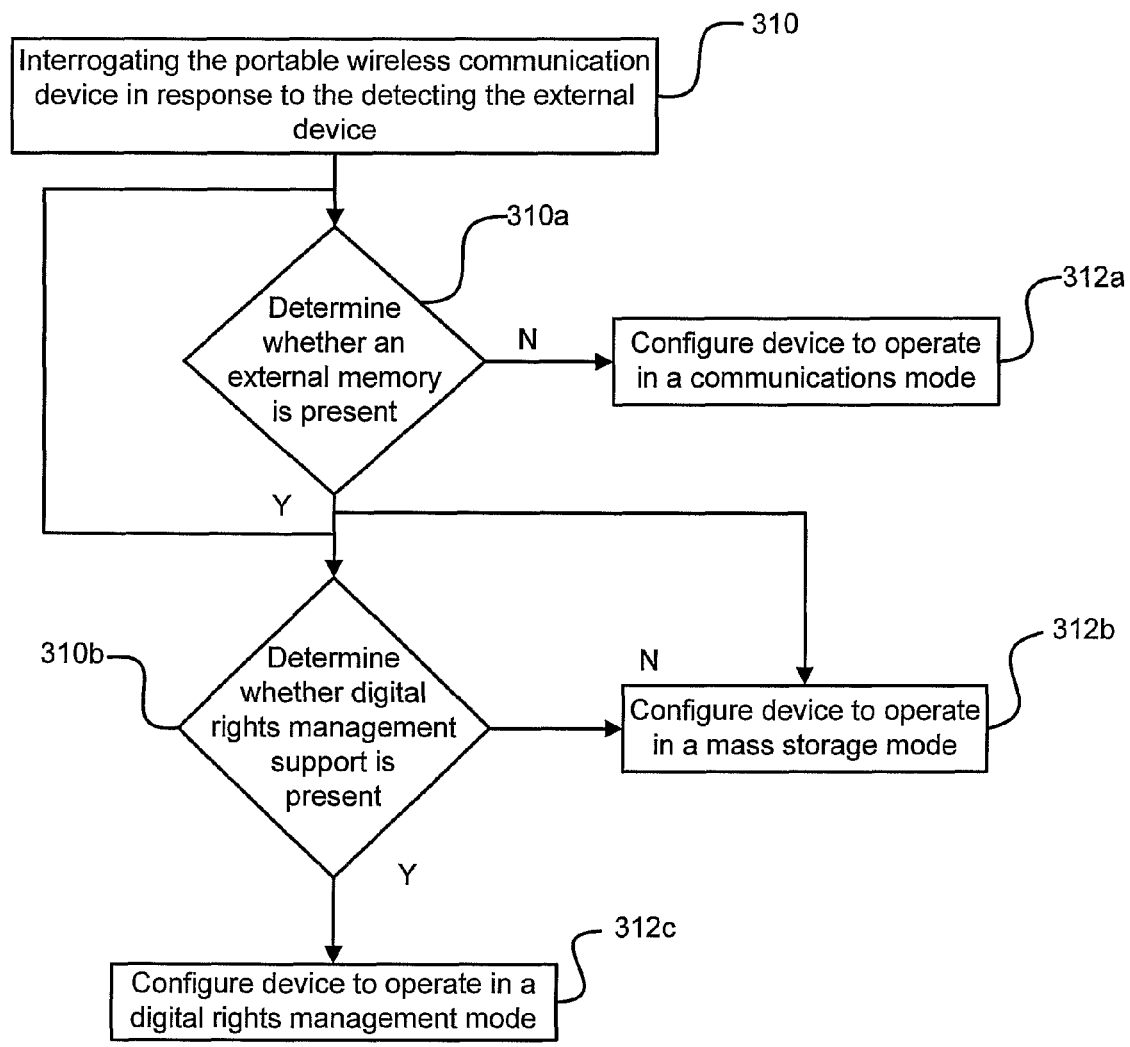
FIG. 3 depicts a method for interrogating the external device and configuring the portable wireless communication device to operate according to a first operating mode.

According to one embodiment, the interrogating step may be further expanded to configure the device in an efficient manner. Referring now to FIG. 3, block 310 corresponds to the interrogation step 210 of FIG. 2, and blocks 312a, 312b, and 312c correspond to the configuration step 212 of FIG. 2. At step 310, the portable wireless communication device interrogates itself in response to the detection of an external device, and the interrogating step may further include determining 310a whether an external memory is present. For example, the portable wireless communication device may interrogate 310 itself to determine 310a whether an insertable memory card present. If no card is present, the portable wireless communication device may configure 312a itself to operate in COM mode, but if a card is present, the portable wireless communication device may then configure 312b itself to operate in MS mode or continue to interrogate itself.

According to another embodiment, the interrogation 310 may include determining 310a whether an external memory is present, as above, and if external memory is present continuing to interrogate itself by determining 310b whether DRM support is present. If no DRM support is present, the portable wireless communication device may then configure 312b itself to operate in a MS mode, and if DRM support is present, the portable wireless communication device may then configure 312c itself to operate in a DRM mode.

By making determination 310a and determination 310b in this order, the portable wireless communication device may configure itself, or remain configured, efficiently without unnecessarily considering operation in other modes. For example, in a portable wireless communication device that would be required to operate in DRM mode where the possibility exists to transfer protected content to a removable media, there is no need to determine whether DRM support is present if no removable media is present in the portable wireless communication device.

According to another embodiment, the interrogation 310 may omit the determination 310a whether an external memory is present, and only determine 310b whether DRM support is present. If no DRM support is present, the portable wireless communication device may then configure itself to operate in COM mode, and if DRM support is present the portable wireless communication device may then configure itself to operate in DRM mode or continue to interrogate itself for additional functionality.

By making these type of determinations, the portable wireless communication device may be customized for varying communication carrier requirements. For example, one carrier may limit access to its protected content where a communication device currently lacks proper license or protective features to access or otherwise use the protected content, whereas another carrier may not provide a user access to protected content. This embodiment would then address each carrier's requirements using the same device.

Additionally, the portable wireless communication device may anticipate, and default to, a statistically likely behavior of a typical user. For example, according to one typical usage profile, the coupling of an external device will most often require the portable wireless communication device to be configured in COM mode, with the next most likely configuration being MS mode. As illustrated above, the configuration decision may be made early on, for example, when determining 310a whether an external memory is present, thus precluding further decisions and preserving device resources.

The foregoing embodiments are illustrative of the various interrogations, but are not limiting. Moreover, the foregoing embodiments are also intended to illustrate that the iterations of interrogating the portable wireless communication device may structured in such a way that reduces the number of logic operations that the portable wireless communication device is required to perform and preferably in a predictive manner.

Figure 4:
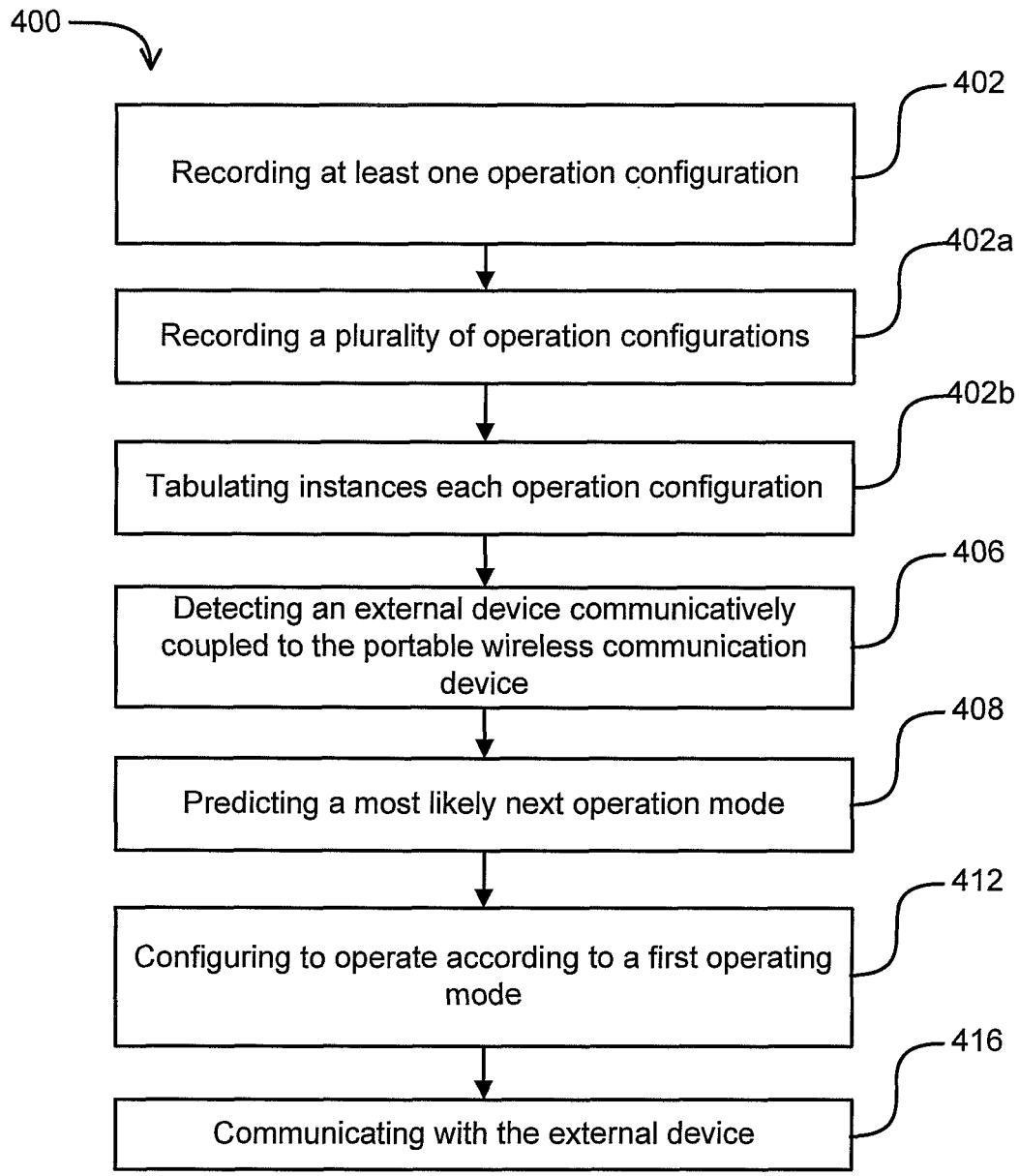
FIG. 4 depicts a method for managing a portable wireless communication device having a plurality of operating modes according to one embodiment of the present invention.

Referring now to FIG. 4, a method 400 for managing a portable wireless communication device having an interface, and configurable to operate in a plurality of operating modes according to one embodiment of the present invention is shown. As above, the method includes detecting 406 an external device communicatively coupled to portable wireless communication device, configuring 412 the portable wireless communication device to operate according to a first operating mode, and communicating 416 with the external device. However, method 400 also includes actively predicting 408 the most likely next operation mode the portable wireless communication device will be used when coupled to the external device. In particular, predicting 408 the most likely next operation mode of the portable wireless communication device may also learn from an individual user's past usage behavior by using any known adaptive learning technique.

By including an adaptive learning mechanism, manufacturers may enjoy flexibility when designing a portable wireless communication device whose usage may vary depending on customer-specific usage scenarios. For example, a device may be optimally designed for a statistically most likely usage profile, yet retain the ability to modify itself according to a particular user's needs. This could be accomplished by initially assigning a default setting or order for automatically configuring the device that, over time will adapt to a particular user's usage pattern. Additionally, the end users will have a positive experience in that no user interaction would be required to update default values of the device, despite what manufacturers set as initial or default values for the device's configuration process.

According to one embodiment, assigning a default setting or order for automatically configuring the device may be accomplished using the self-interrogation technique of FIG. 3 and as discussed above. Additionally, the portable wireless communication device may be reset to its defaults periodically or upon the occurrence of an event, such as when a second user uses the device.

According to one embodiment, the method 400 for managing a portable wireless communication device may further include recording 402 at least one operation configuration. It is understood that recording 402 at least one operation configuration may also include recording 402a a plurality of operation configurations. By way of illustration, recording 402a may include recording 402a an instance that the portable wireless communication device was configured to operate in COM mode. On another occasion, the recording 402a may include recording an instance that the portable wireless communication device was configured to operate in DRM mode. Recording may be done prior to configuration, during configuration, of subsequent to configuration of the device. In this way the device begins to develop a history of its actual usage, as compared to an initially expected usage.

Additionally, recording 402 at least one operation configuration may include tabulating 402b instances of each operation configuration, typically storing such information in a memory, such as non-volatile memory, for example. It is understood that tabulating 402b instances of each operation configuration is not limited to any particular tabulation technique, but need only add some predictive value to the recording 402 of at least one operation configuration. To Illustrate tabulating 402b instances of each operation configuration, tabulating may include assigning a value or weight to each of the plurality of operating modes, with each assigned value representing the likelihood of its respective mode being the next operation mode. The device may then modify the value assigned to the operating mode associated with the recorded operation configuration. Thus the tabulating may further include associating a weight to each operation mode such that each time the portable wireless communication device is configured according to particular operating mode, the value representing that configuration may be increased.

According to one particular embodiment, the portable wireless communication device may keep a running tally of the number of times the portable wireless communication device was configured to operate in each operating mode available. Accordingly, as the portable wireless communication device is increasingly used under a particular operating mode the weight assigned to the operating mode may be increased.

According to another embodiment, the portable wireless communication device may predict 408 the most likely next operation mode in response to the recorded 402 operation configuration. Predicting typically includes considering prior operating modes selected or utilized. Moreover, predicting 408 may include additional considerations as well. For example, rather than using the default settings discussed above as merely a starting point, the device may continually compare the prior operating modes selected or utilized to the device's default settings. This may be accomplished using any appropriate predetermined weighting scheme.

Accordingly, the portable wireless communication device may then configure 412 the portable wireless communication device to operate according to the first operating mode in response to predicting 408 the most likely next operation mode. Once configured, the device may communicate 416 with the external device according to the desired operation mode.

According to one alternate embodiment, the portable wireless communication device may predict 408 the most likely next operation mode of multiple users. In particular, the adaptive learning mechanism may provide for segregation of learned behaviors according to which user is using the portable wireless communication device. The may be accomplished by any number of known means. For example, the learned behaviors may be associated with a user's login or identification information. Alternatively, the learned behaviors may be associated with a profile in which multiple users fall into one category. For example, the "owner" of the portable wireless communication device may have one profile, whereas "guests" may have another profile.

The above embodiments are understood to be illustrative, and variations to the automatic self-configuration of the portable wireless communication device are contemplated. For example, as discussed above, the portable wireless communication device may be configured to states and operation modes other than those mentioned.

Additionally, the adaptive learning mechanism need not be persistent in some embodiments. According to certain embodiments, it may be disabled as required, for example by a user, by a manufacturer, or by a carrier.

Although the invention has been presented in the context of operation modes typical of a mobile phone, it should be understood that the invention has wider application, and may vary with the functionality of the device incorporating the invention. Further, although specific arrangements of selecting and predicting operation modes have been presented, it should be understood that alternate arrangements and combinations of the features are contemplated for use with the present invention. Other variations and embodiments of the invention will occur to those skilled in the art.

What is claimed is:

1. A computer-implemented method for managing the portable wireless communication device, where one or more processors are programmed to perform the steps comprising:
    detecting an external device communicatively coupled to the portable wireless communication device, the external device being communicatively coupled through the interface;
    configuring the portable wireless communication device to communicate with the external device based on tabulating information pertaining to past usage behavior, the past usage behavior being tabulated from instances of past operation configurations of the portable wireless communication device and assigned a weight value representing a given operation configuration mode's likelihood of being the next operation mode; and in response to detecting the external device communicatively coupled to the portable wireless communication device, performing the following:

determining whether an external removable memory is coupled to the portable wireless communication device;

configuring a port of the portable wireless communication device and operating the portable wireless communication device in a communications mode if the removable memory is not present;

determining whether the portable wireless communication device supports digital rights management if the removable memory is present;

configuring the portable wireless communication device to operate in a mass storage mode if the removable memory is present and the portable wireless communication device does not support digital rights management; and configuring the portable wireless communication device to operate in a digital rights management mode if the removable memory is present and the portable wireless communication device does support digital rights management.

2. The method of claim 1, further comprising:

predicting a most likely next operation mode responsive to the past usage behavior based on the information tabulated.

3. The method of claim 2, further comprising:

automatically configuring the portable wireless communication device to operate according to a first operation mode responsive to the predicting step.

4. The method of claim 3, wherein the predicting step further comprises:

assigning a value to each of the following plurality of operation modes: the communications mode, the mass storage mode, and the digital rights management mode, each assigned value representing the likelihood of its respective operation mode being the next operation mode; and modifying the value assigned to the operation mode associated with the first operation configuration.

5. The method of claim 4, wherein the modifying step further comprises increasing the value assigned to the operation mode associated with the first operation configuration, the predicting step further comprising selecting the operation mode having the highest assigned value.

6. The method of claim 4, further comprising assigning a default value to each of the plurality of operation modes, the predicting step being responsive to the assigned default values for each of the plurality of operation modes.

7. The method of claim 6, further comprising interrogating the portable wireless communication device in response to the detecting the external device, the assigning step being responsive to the interrogating the portable wireless communication device.

8. The method of claim 2, wherein the predicting step further comprises predicting the most likely next operation mode of a first user and of a second user.

9. The method of claim 2, wherein the predicting step further comprises predicting the most likely next operation mode of a first user and of a first class of user.

* * * * *